US006668073B1

(12) United States Patent
Robar et al.

(10) Patent No.: US 6,668,073 B1
(45) Date of Patent: Dec. 23, 2003

(54) ANTHROPOMORPHIC FILM PHANTOM FOR THREE-DIMENSIONAL DOSIMETRY

(75) Inventors: James L. Robar, Vancouver (CA); Brenda G. Clark, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/436,917

(22) Filed: Nov. 9, 1999

Related U.S. Application Data
(60) Provisional application No. 60/108,281, filed on Nov. 12, 1998.

(51) Int. Cl.[7] .................................................. G06K 9/00
(52) U.S. Cl. ...................................................... 382/128
(58) Field of Search ................................ 378/174, 207, 378/64, 204, 167, 18; 382/128; 250/336.1, 370.07, 252.1, 337, 484.3, 580, 584, 585, 586

(56) References Cited

U.S. PATENT DOCUMENTS

| 5,207,223 A | | 5/1993 | Adler |
| 5,250,019 A | | 10/1993 | McGinley |
| 5,339,347 A | | 8/1994 | Slatkin et al. |
| 5,430,308 A | | 7/1995 | Feichtner et al. |
| 5,511,107 A | | 4/1996 | Sliski |
| 5,633,584 A | | 5/1997 | Maryanskl et al. |
| 5,635,709 A | | 6/1997 | Sliski et al. |
| 5,651,046 A | | 7/1997 | Floyd et al. |
| 5,661,310 A | | 8/1997 | Jones |
| 5,703,370 A | * | 12/1997 | Kronenberg et al. ........ 378/174 |
| 6,309,352 B1 | * | 10/2001 | Oraevsky et al. ........... 378/207 |

OTHER PUBLICATIONS

Slatkin, D.N., et al., "Microbeam Radiation Therapy," *Medical Physics*, vol. 19, No. 6, Nov./Dec. 1992, pp. 1395–1400.

\* cited by examiner

*Primary Examiner*—Leo Boudreau
*Assistant Examiner*—Tom Y. Lu
(74) *Attorney, Agent, or Firm*—Oyen Viggs Green & Mutala (57) ABSTRACT

A method and system for recording and verifying three-dimensional dose distributions administered during stereotactic radiosurgery using an anthropomorphic film phantom are provided. The method provides a phantom (11) including a head-shaped hollow shell (12), which mounts a cassette-box therein (14), which in turn may contain a simulated lesion (16) similar to the lesion to be treated. An image is taken of the head-shaped shell including the cassettebox and the simulated lesion using, for example, a CT or MRI scanner. The image is used to develop a stereotactic radiosurgery plan, which includes creating an intended three-dimensional dose distribution map to "treat" the simulated lesion. Thereafter, the simulated lesion is removed from the cassettebox and the cassettebox is loaded with multiple layers of film (42) separated by spacers (44) having tissue-equivalent characteristics. Then, the three-dimensional radiation dose described by the stereotactic radiosurgery plan is delivered to the head-shaped shell including the cassettebox loaded with the film. Next, the multiple layers of film are removed from the cassettebox, and multiple dose images are obtained based on the film. Thereafter, based on the multiple dose images, a measured three-dimensional dose distribution map is obtained. The measured three-dimensional dose distribution map is coregistered in software with the intended three-dimensional dose distribution map that was previously developed, to ascertain any discrepancies therebetween to determine inaccuracies included in the original stereotactic radiosurgery plan.

24 Claims, 5 Drawing Sheets

ANTHROPOMORPHIC FILM PHANTOM FOR THREE-DIMENSIONAL DOSIMETRY

CROSS-REFERENCE TO RELATED APPLICATION

The present application claims the benefit under 35 U.S.C. § 119(e) of the filing date of U.S. provisional application Ser. No. 60/108,281, filed Nov. 12, 1998.

FIELD OF THE INVENTION

The present invention relates to a method and system for recording and verifying three-dimensional radiation dose distributions using an anthropomorphic film phantom.

BACKGROUND OF THE INVENTION

Stereotactic radiosurgery is a method for treating brain lesions, using collimated convergent beams of x-ray photons produced by a clinical linear accelerator. In order to conform the administered dose distribution to the delineated volume of the lesion, while sparing healthy adjacent tissue, the method requires an extremely high spatial accuracy of approximately ±1 millimeter (mm). The method also requires an accuracy of ±2% in controlling the magnitude of the administered dose.

Because the success of stereotactic radiosurgery hinges on the accurate delivery of dosage of x-ray photons to the lesion, simulated radiosurgery using a suitable phantom, or a pseudo-object, is performed prior to actual application of the radiosurgery to a human patient, to record and verify the resulting dose distribution. The result of the simulated radiosurgery may be used to adjust stereotactic radiosurgery parameters to ensure that the desired dose distribution is applied to a human patient. Currently, ionization chambers, diodes, and diamond detectors are used to measure radiation dose distribution. (See, for example, U.S. Pat. No. 5,635,709.) Unfortunately, such devices provide a dose measurement at a single point at a time. Alternatively, radiosensitive polymer gels have been used as prototypical three-dimensional dosimeters as described, for example, in U.S. Pat. No. 5,633,584. Unfortunately, such gels are not well established, and require an expensive magnetic resonance imaging (MRI) scanner in order to read the recorded dose distribution.

SUMMARY OF THE INVENTION

The present invention provides a method and system for recording and verifying a dose of radiation to be administered to a subject in three dimensions simultaneously, using an anthropomorphic Film phantom. The method and system offer high spatial resolution, and the capacity to integrate over time the dose produced by multiple beams.

The phantom of the invention includes a hollow shell in the form of, for example, a human head, which is made of tissue-equivalent material and filled also with tissue-equivalent material. The phantom also includes a box made of tissue-equivalent material, which is adapted to be adjustably securable within the hollow shell. The phantom further includes multiple layers of film separated by multiple spacers, which are replaceably loaded into the box.

According to the method of the present invention, first, the hollow shell is provided. Mounted in the hollow shell is the box. Next, an image of a lesion to be treated is registered into treatment-planning software. For this purpose, an image or three-dimensional contour of an actual lesion may be transferred to the software. Alternatively, a simulated lesion modeled after an actual lesion may be formed and secured in the box, which is adjustably positioned and secured within the hollow shell, and an image may be taken of the hollow shell including the box that contains the simulated lesion. To take an image of the simulated lesion, a computed tomography (CT) or magnetic resonance imaging (MRI) scanner may be used. The image of the simulated lesion is then transferred to the treatment-planning software, and the simulated lesion is removed from the box. Next, the image of a lesion thus registered in the software is used to develop a stereotactic radiosurgery plan, and an intended three-dimensional dose distribution map is created to treat the lesion.

After the plan is developed, the box is loaded with multiple layers of film separated by spacers having tissue-equivalent characteristics. Thereafter, the three-dimensional radiation dose described by the stereotactic radiosurgery plan is delivered, while the hollow shell is supported by a head ring in a target-positioner box. Both the head ring and the target-positioner box are commonly used clinical components. Then, the multiple layers of film are removed from the box. If preferable to increase spatial resolution of the final measured dose distribution map, the box may be again loaded with multiple layers of unexposed film and the three-dimensional dose may be delivered thereto, with the angle of the box varied with respect to the hollow shell. These steps may be repeated a suitable number of times to obtain plural sets of multiple layers of film, all of which include the radiation dose recorded thereon. Thereafter, multiple dose images are obtained based on the multiple layers of film. Based on the multiple dose images, a measured three-dimensional dose distribution map is obtained. Thereafter, the measured three-dimensional dose distribution map is coregistered in the treatment-planning software with the intended three-dimensional dose distribution map that was previously developed, to ascertain any discrepancies therebetween to determine inaccuracies included in the original stereotactic radiosurgery plan.

In accordance with one aspect of the present invention, the box is supported by a rod, and the rod is slidably adjustable along its longitudinal axis to vary the position of the box along the axis within the hollow shell.

In accordance with another aspect of the present invention, the box is made of material opaque to visible light except for a diagonal strip that is made of material translucent to visible light. When the multiple layers of radiographic film loaded in the box thus constructed are exposed to radiation, indexing marks are recorded on the edges of the film, each film having a unique indexing mark. The indexing marks may be advantageously used to automatically orient and order the multiple layers of film.

The phantom system and method of the present invention record and verify a dose administered during stereotactic radiosurgery in three dimensions simultaneously. Because the system and method are designed to closely simulate the complete process of actual stereotactic radiosurgery performed on a patient, any spatial error included in each step of actual radiosurgery can be thoroughly encompassed in the simulation method of the present invention. The system and method, thus, allow for accurately adjusting a stereotactic radiosurgery plan based on the simulation result, prior to its actual application on a patient.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Stereotactic radiosurgery performed on patients in clinical settings typically involves the following steps (1) through (6), wherein each step introduces its own spatial uncertainty. The present invention provides a simulation method and system for recording and verifying three-dimensional dose distributions, which closely model the actual stereotactic radiosurgery, so as to quantify each of these uncertainties. (1) A head ring (typically metal) is attached to encircle a patient's skull. (2) A localizer box is attached to the head ring. The localizer box is a plastic box that clips securely onto the head ring and fits around the patient's head. On the faces of this box are marks, which are identifiable in CT images in order to establish a coordinate system in which the position of the patient's lesion is defined. (3) The patient's head is imaged using a CT or MRI scanner. (4) Based on the acquired images of the head and the lesion, an appropriate arrangement of the treatment beam is established using commercially available treatment-planning software. (5) A target-positioner box replaces the localizer box on the head ring. The target-positioner box is similar to the localizer box, except that it is used to accurately position the patient on the linear accelerator couch used in stereotactic radiosurgery. Attached to the faces of the target-positioner box are marks, which are used for aligning the patient with fixed reference laser beams. (6) The treatment is administered using a number of beams of x rays generated by the linear accelerator.

To accurately simulate actual stereotactic radiosurgery, as outlined above in steps (1) through (6), the method and system of the present invention have been developed for recording and verifying three-dimensional dose distributions using an anthropomorphic film phantom in a form completely compatible with all the clinically used equipment (head ring, localizer box, target-positioner box, various medical 10 imaging scanners, etc.).

Figure 1:
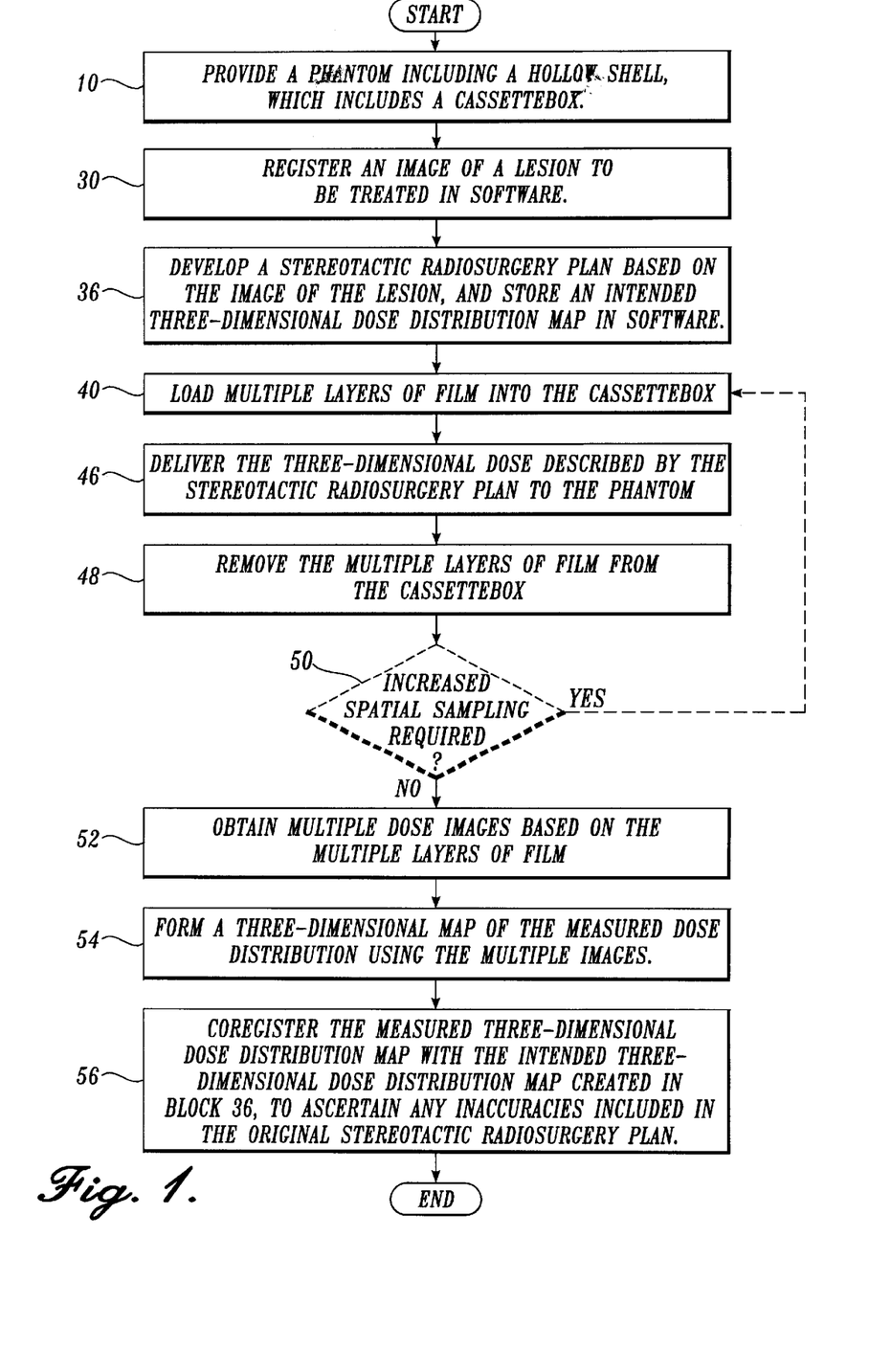
FIG. 1 is a flowchart of a method of recording and verifying three-dimensional dose distributions using a phantom in accordance with the present invention.
Figure 2:
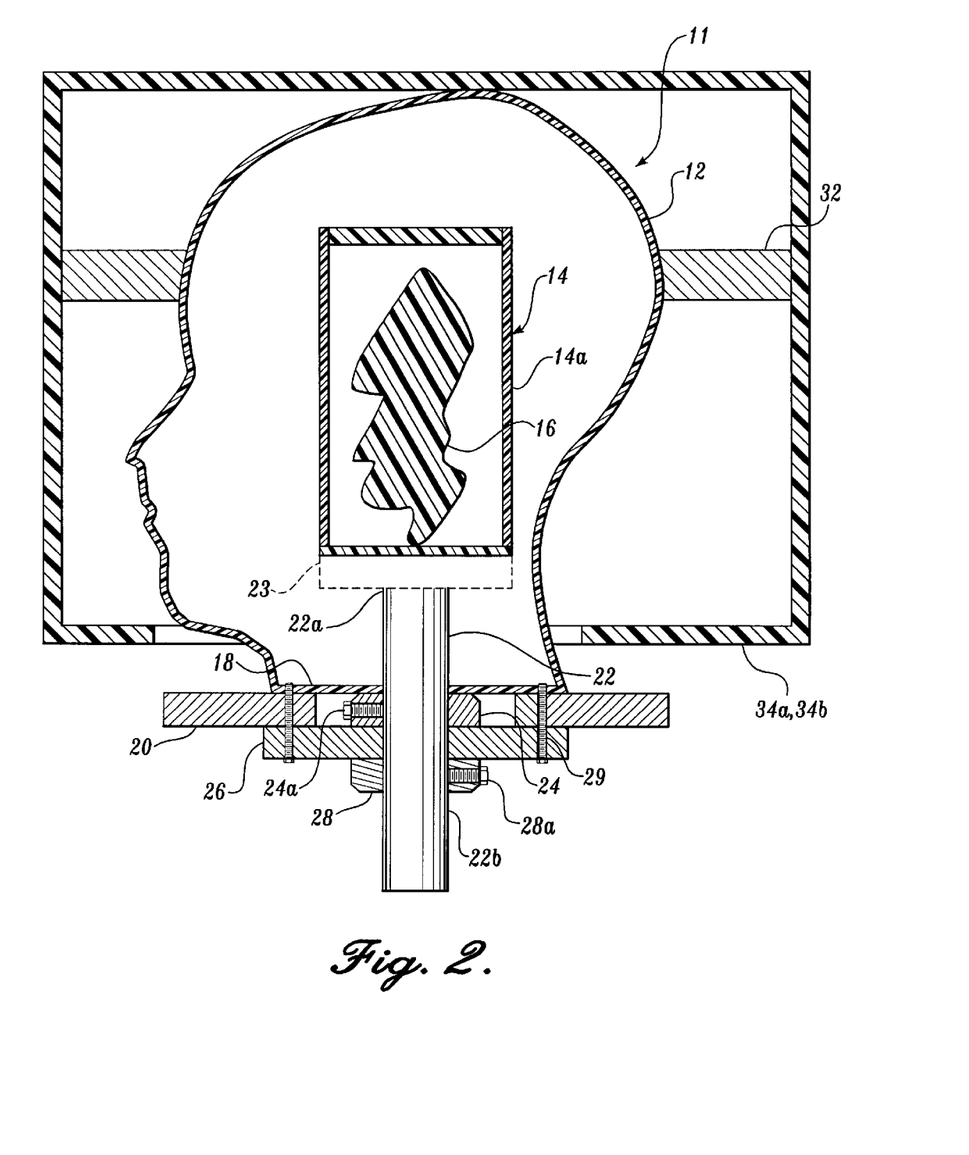
FIG. 2 is a cross-sectional view of a phantom including a head-shaped hollow shell and a box containing a simulated lesion, suitable for use in the present method.

Specifically, FIG. 1 is a flowchart illustrating the steps involved in the method of the present invention using a phantom. Referring additionally to FIG. 2, first, as indicated in box 10 of FIG. 1, a phantom 11 including a hollow shell 12 is provided, which houses a box or cassettebox 14.

The hollow shell 12 is configured so as to closely simulate a human head in terms of the head's treatment (i.e., how the head is supported, imaged, treated, etc.) throughout the entire process of stereotactic radiosurgery. Thus, as illustrated in FIG. 2, the hollow shell 12 is preferably in the shape of an average human head. While in the following description the hollow shell 12 is referred to as "head-shaped shell 12" for convenience, it is to be understood that the hollow shell 12 may take other shapes, such as spherical and light-bulb shapes, as long as the shape accurately simulates a human head during radiosurgery. The head-shaped shell 12 is made of plastic, for example, or any other suitable material that has tissue-equivalent characteristics. A neck 18 of the head-shaped shell 12 is open and is supported by a ring-shaped neck plate 20, which is in turn supported by a neck cover plate 26. In use, the head-shaped shell 12 is filled with material that simulates brain tissue, such as water. Water is considered tissue equivalent because it closely resembles tissue in terms of effective atomic number, density, and electron-density, which are all factors that affect absorption and attenuation of x rays.

Figure 3:
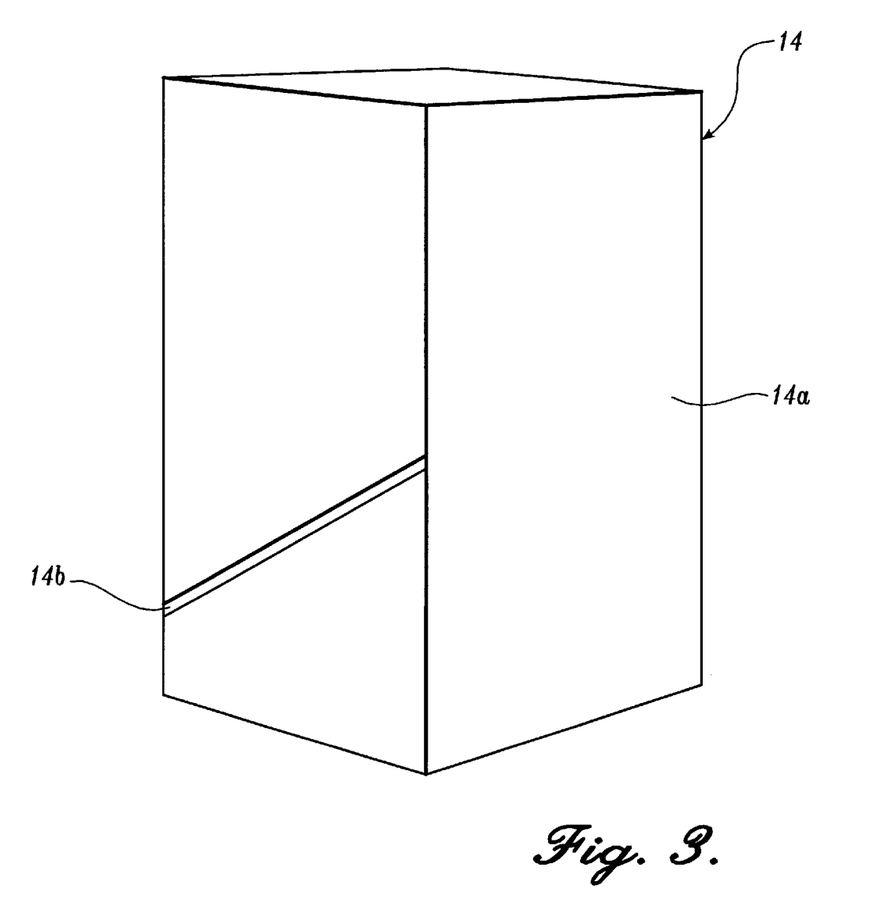
FIG. 3 is a perspective view of the box of FIG. 2.

The head-shaped shell 12 is adapted to adjustably position and mount the cassettebox 14. Referring additionally to FIG. 3, the cassettebox 14 is made of suitable material having tissue-equivalent characteristics, for example, plastic such as polystyrene, Solid Water® available from Gammex, Inc. of Wisconsin, USA; Plastic Water® available from Computerized Imaging Reference Systems, Inc. of Virginia, USA; and Lucite® available from E. I. Du Pont de Nemours & Co. of Delaware, USA. Preferably, the cassettebox 14 is made of opaque material, or outer walls 14a of the cassettebox 14 are covered with a tissue-equivalent coating or veneer that is opaque to visible light, except for a diagonal strip 14b provided on one wall of the cassettebox 14. The strip 14b is also made of tissue-equivalent material, such as translucent polystyrene. Construction of the cassettebox 14 as illustrated in FIG. 3 is advantageous for indexing each of multiple layers of radiographic film loaded in the cassettebox, as more fully described below.

Returning to FIG. 2, the cassettebox 14 is inserted through the open neck 18 of the head-shaped shell 12 and is adjustably positioned therein. To this end, the cassettebox 14 is supported on one end 22a of a rod 22 via an attachment mechanism 23. Any mechanism that securely attaches the rod end 22a to the cassettebox 14 may be used. For example, the rod end 22a may be threaded, bolted, or adhered to the cassettebox 14. The other end 22b of the rod 22 passes through a first bushing 24, the neck cover plate 26, and a second bushing 28, which all include centrally located apertures to allow insertion of the rod 22 therethrough. The first and second bushings 24, 28 include first and second set screws 24a, 28a, respectively. Thus constructed, the position of the cassettebox 14 can be freely adjusted vertically within the head-shaped shell 12 by sliding the rod 22 along its longitudinal axis, and the position of the cassettebox 14 can be secured at a preferred location by using the set screws 24a, 28a to tighten the first and second bushings 24, 28. It is also noted that by axially rotating the rod 22, the angular orientation of the cassettebox 14 with respect to the head-shaped shell 12 can also be adjusted throughout the 360° range. To accurately adjust the angular orientation of the cassettebox 14, the neck cover plate 26 may have angular gauge indicia, as on a protractor.

The head-shaped shell 12, the neck plate 20, and the neck cover plate 26 are assembled together using any suitable means, such as one or more bolts 29. By assembling and disassembling these components, the cassettebox 14 can be freely inserted into and removed from the head-shaped shell 12.

Alternatively, or additionally, to the vertical and angular adjustment of the cassettebox 14 with respect to the head-shaped shell 12 as described above, the cassettebox 14 may be adapted to allow for other types of adjustment. For example, the attachment mechanism 23 may include a slotted arm extending generally perpendicularly from the rod end 22a to couple the cassettebox 14 to the rod 22 so that the cassettebox 14 can be adjustably positioned off the longitudinal axis of the rod 22. As a further example, the attachment mechanism 23 may include a plastic universal ball-joint to couple the cassettebox 14 and the rod end 22a together so that the cassettebox 14 can be freely rotated or tilted with respect to the rod 22. Various other types of attachment mechanisms 23 for positioning the cassettebox 14 at any desired location inside the volume of the head-shaped shell 12 may be used.

Next, as indicated in block 30 of FIG. 1, an image of a lesion to be treated, including the lesion's relative position with respect to the head-shaped shell 12, is registered in treatment-planning software. Any commercially available treatment-planning software may be used, such as BrainSCAN® available from BrainLAB Medical Computersysteme GmbH of Germany and XPlan® available from Radionics, Inc. of Massachusetts, USA. Various methods may be used to register the image of a lesion in the software. For example, an image or three-dimensional contour of the actual lesion in a patient may be transferred to the software, as routinely done in the art.

Alternatively, a simulated lesion 16 (see FIG. 2) that models the actual lesion to be treated may be prepared. The simulated lesion 16 is made of material that is visible in CT and MRI images, for example, plastic or wax. By molding plastic or wax, one may freely form a lesion of various sizes and shapes to simulate a variety of actual lesions encountered in clinical settings. The simulated lesion 16 is then securely positioned within the cassettebox 14 using any suitable means (for example, providing a small pin that passes into both the cassettebox 14 and the simulated lesion 16). The rest of the cassettebox 14 is filled with tissue-equivalent material such as water. Thereafter, the cassettebox 14 is secured at a predetermined position within the head-shaped shell 12, so that the simulated lesion 16 will occupy the same position with respect to the head-shaped shell 12 as the position that the actual lesion occupies with respect to the actual human head. Next, an image of the head-shaped shell 12 including the cassettebox 14 containing the simulated lesion 16 is taken, using, for example, a CT or MRI scanner. The image of the simulated lesion 16 is then transferred to the treatment-planning software.

The method of taking a CT or MRI image is well known in the art and, thus, is not described in detail here. It is to be noted, however, that the head-shaped shell 12 is advantageously supported by a head ring 32 and an outer localizer box 34a when the image of the simulated lesion 16 is taken. The head ring 32 is a common clinical device used to encircle and support a human skull when the head needs to undergo certain scanning or radiosurgical operations. Since the head-shaped shell 12 is modeled after an average human head, the head ring 32 may be used to support the head-shaped shell 12 to simulate actual image taking. The head ring 32 is typically attached to the phantom 14 using a plurality of carbon fiber or metallic pins. The localizer box 34a, typically, is also a commonly used clinical component that is adapted to be coupled to the head ring 32 to accurately position a human head (or a head-shaped shell in the present case). The localizer box 34a includes marks thereon that are used during the imaging of the head-shaped shell 12 as reference points in order to accurately define the location of the simulated lesion 16. Once the image of the simulated lesion 16 is taken, the cassettebox 14 is removed from the head-shaped shell 12 and the simulated lesion 16 is removed from the cassettebox 14. Also, the localizer box 34a is removed from the head ring 32.

Next, as indicated in block 36 of FIG. 1, a stereotactic radiosurgery plan, including an intended three-dimensional dose distribution map, is developed in the treatment-planning software based on the registered image of the lesion. The intended dose distribution map developed is registered in the treatment-planning software. The method of creating and registering a three-dimensional dose distribution map is well known in the art and, thus, is not described in the present application.

Then, as indicated in block 40 of FIG. 1, multiple layers of radiation-sensitive film 42, for example, radiographic film or radiochromic film, are loaded into the cassettebox 14. See FIG. 4 additionally. Each film (typically approximately 0.2 mm thick) is separated from each adjacent film by a spacer 44 having tissue-equivalent characteristics, such as any suitable plastic including polystyrene, Solid Water®, Plastic Water®, and Lucite®. The film 42 and the spacers 44 are layered together without leaving an air gap therebetween, so that the assembly of the film and the spacers will have tissue-equivalent characteristics. The thickness of the spacer 44 is to be determined based on various factors. To increase spatial resolution, more sheets of the film 42 should be used, and the thickness of the spacers 44 should be decreased accordingly so that all the film can be loaded into the cassettebox 14 having a given volume. At the same time, however, the number of sheets of the film 42 should not be exorbitant, so that the time required for processing all the film will not be excessive. Typically, commercially available polystyrene sheets have a thickness of approximately ⅛" (3.2 mm). This thickness has been found to be adequate for the spacers 44 to meet all the requirements as described above, to be suitable for use in the present invention.

It is noted that any radiation-sensitive film suitable for recording dose distribution may be used. Radiographic film, such as Kodak X-Omat V film, may be advantageous in some situations because it is readily available in all radiation oncology centers, is affordable, and records the given dose with extremely high spatial resolution in two dimensions in the plane of the film. In other situations, radiochromic film may be used instead. Radiochromic film includes one or more microcrystalline monomeric layers that polymerize in response to exposure by radiation and, thus, unlike radiographic film, does not require chemical processing.

Figure 4:
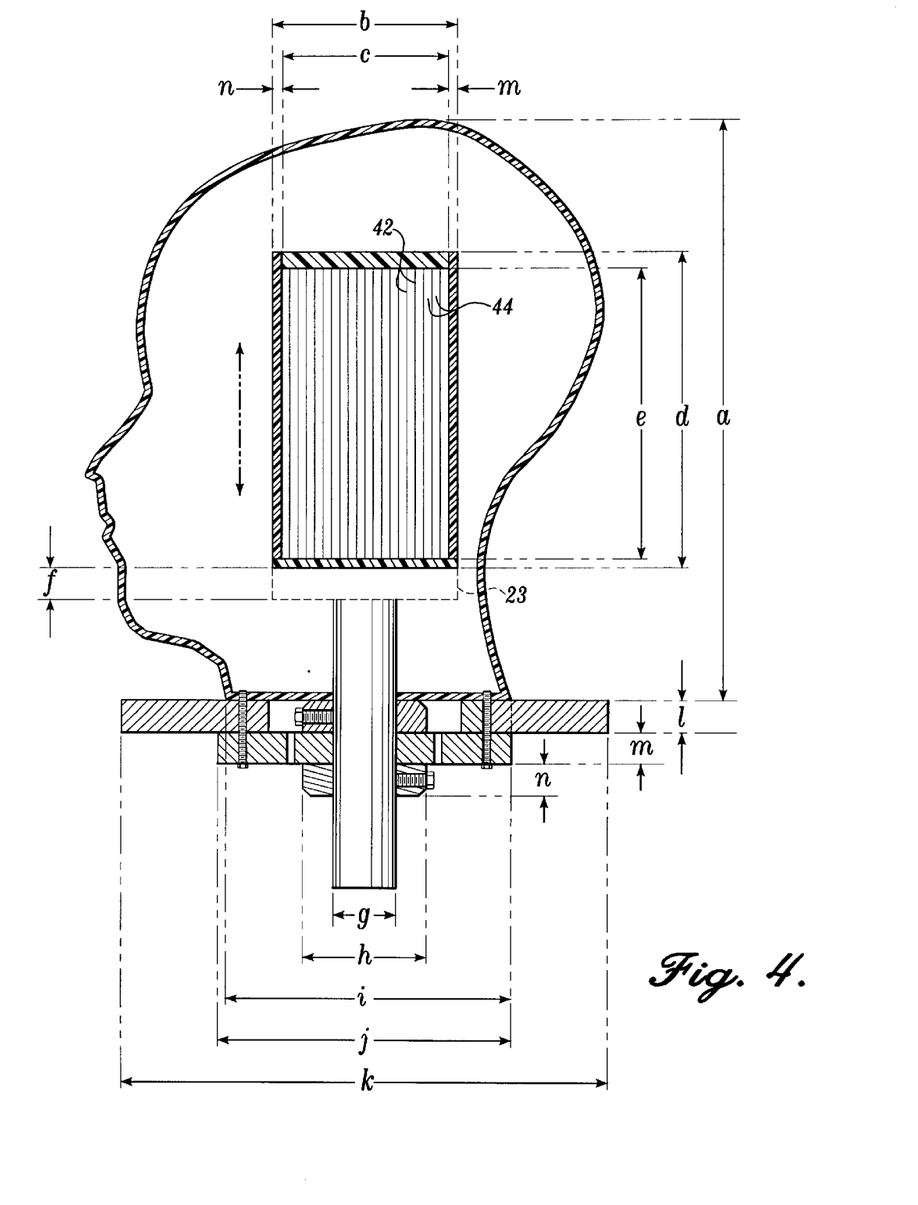
FIG. 4 is a cross-sectional view of the head-shaped hollow shell and the box of FIG. 2, containing multiple layers of film instead of the simulated lesion.

Once loaded with the film 42 and the spacers 44, the cassettebox 14 is inserted into the head-shaped shell 12 and securely positioned therein. The cassettebox 14 is positioned at the same location where the cassettebox 14 containing the simulated lesion 16 was previously situated with respect to the head-shaped shell 12, or where an actual lesion was situated with respect to a human head.

Next, as indicated in block 46 of FIG. 1, the three-dimensional radiation dose is delivered as described by the stereotactic radiosurgery plan (developed in block 36) to the head-shaped shell 12. At this time, the head-shaped shell 12, including the cassettebox 14 containing the film 42, is supported by the head ring 32, and by an outer target-positioner box 34b attached to the head ring 32. The target-positioner box 34b and the localizer box 34a take similar outer forms and, thus, both boxes 34a, 34b are represented by a single box illustrated in FIG. 2. The target-positioner box 34b, similarly to the localizer box 34a described above, is a known piece of equipment that is routinely used in stereotactic radiosurgery. Specifically, a paper printout of marks generated based on the intended three-dimensional dose distribution map is accurately positioned on the target-positioner box 34b. The target-positioner box 34b thus permits the alignment of the lesion with the isocenter (i.e., focus) of the linear accelerator used in stereotactic radiosurgery.

It is to be noted that different sizes of the film 42 can be included in the cassettebox 14 depending on each application, as long as the film is loaded into a cassettebox having the inner dimensions that closely match the particular film size to eliminate any air gaps. For example, relatively large sheets of film (12.0 cm×7 cm, for example) may be used to record relatively large radiosurgical dose distributions, which are also large enough to be fed into typical automatic film processors, as more fully described below. Alternatively, relatively small sheets of film (6 cm×6 cm, for example) may be used, which are still large enough to record typical radiation dose distributions but may need to be attached to film leaders to be fed into conventional automatic processors.

In FIG. 4, dimensions of the head-shaped shell 12, the cassettebox 14, the rod 22, and other parts described above are indicated as "a" through "n". It has been found that in one embodiment of the present invention adapted to accommodate film sized 12.0 cm×7 cm, the inner dimensions of the cassettebox 14 can be 7 cm×7 cm×12 cm, and the dimensions can be a=24.37, b=7.64, c=7.00, d=12.95, e=12.00, f=1.27, g=2.54, h=5.00, i=11.76, j=12.00, k=20.00, l=1.27, m=1.27, and n=1.27, respectively, all in centimeters (cm). In another embodiment adapted to accommodate film sized 6 cm×6 cm, the inner dimensions of the cassettebox may be 6 cm×6 cm×6 cm, and the dimensions "b" through "e" may be changed from above to b=6.64, c=6.00, d=6.95, and e=6.00, respectively, all in centimeters. These latter dimensions may be appropriate when radiochromic film is used, since this film is typically supplied with dimensions of 12.7 cm×12.5 cm and, thus, four sheets of film of roughly 6 cm×6 cm can be cut from one sheet of radiochromic film.

It should be understood, though, that the dimensions may be readily modified according to a specific application of the present invention, and are not limited to the specific examples given above. For example, the dimensions of the cassettebox 14 may be freely modified according to the maximum size of the dose distribution to be measured or the maximum size of the film to be used. Further, multiple casseteboxes of different sizes may be provided, and used interchangeably depending on the particular needs of each application.

After the three-dimensional radiation dose is delivered to the film phantom, next, as indicated in box 48 of FIG. 1, the film 42 is removed from the cassettebox 14.

Figure 5A:
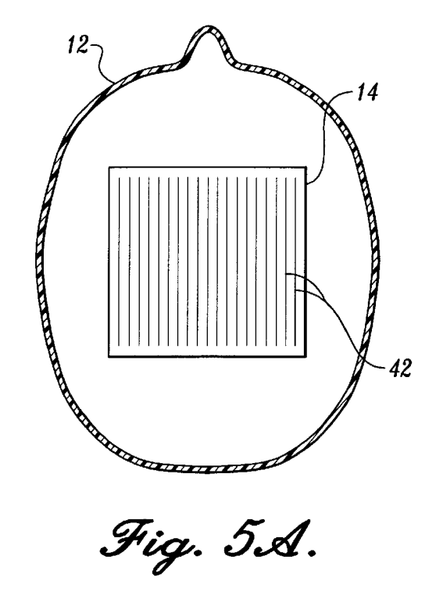
FIGS. 5A, 5B, and 5C are corresponding schematic top views of a head-shaped hollow shell including a box containing multiple layers of film, wherein the angular orientation of the box with respect to the head-shaped hollow shell is varied.
Figure 5B:
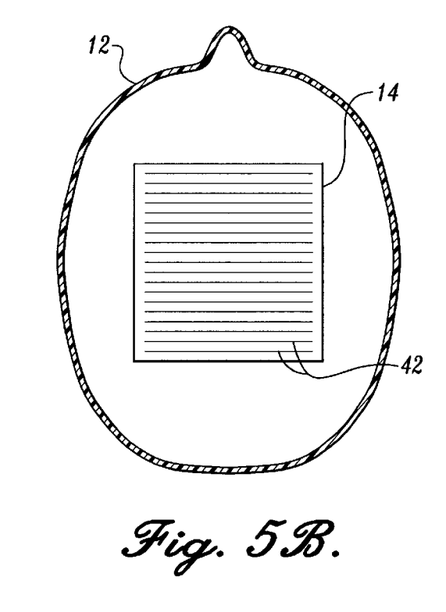
Figure 5C:
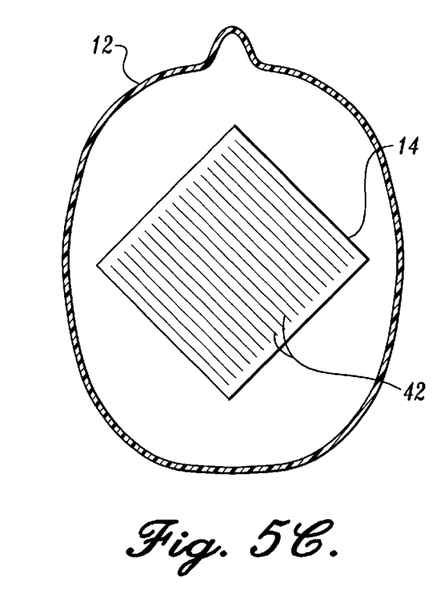

As indicated in box 50 of FIG. 1, optionally, it is determined if increased spatial sampling is required in order to improve the spatial resolution of the final three-dimensional dose distribution map. If so, the method returns to box 40, and repeats the steps of blocks 46 and 48 by varying the angular orientation of the cassettebox 14 with respect to the head-shaped shell 12. The loop may be repeated for a suitable number of times, by each time varying the angular orientation of the cassettebox 14. For example, in FIG. 5A, the dose distribution is first recorded with the film 42 plane along saggital planes. Then, in FIG. 5B, the cassettebox 14 is rotated 90 degrees from FIG. 5A, reloaded with unexposed film, and the dose distribution is recorded along coronal planes. Thereafter, in FIG. 5C, the cassettebox 14 is reloaded with another set of film and rotated to position the film planes at 45 degrees between the coronal and saggital planes. Plural sets of multiple layers of film 42 can then be used to obtain plural sets of multiple images of dosage later, which can be combined to improve spatial resolution of the final measured three-dimensional dose distribution map. When plural sets of multiple images are taken, the resolution is ultimately limited only by the resolution achievable in scanning the film (approximately 0.05 mm).

Thereafter, as indicated in box 52 of FIG. 1, multiple dose images can be obtained based on the multiple layers of film 42. Specifically, the layers of film 42 are processed using a standard film processor, as well known in the art. A film processor uses chemicals to perform the development, fixing, washing, and drying of the latent image recorded on the film 42. (The chemical processing step is not required if radiochromic film is used.) Next, the film 42 is digitized to form multiple images of the optical density pattern recorded on the film, using any suitable optical densitometer or scanner, also as well known in the art. Thereafter, using any suitable image processing software, the digitized optical density images are converted to images reflecting the dose administered at the location of each layer of the film 42 based on the sensitometric curve for the film 42, as well known in the art.

For the multiple dose images thus obtained to be later combined to form a three-dimensional dose distribution map, as described below, they need to be properly oriented and ordered. Orienting and ordering are preferably done automatically in the image processing software. To this end, it is advantageous to construct the cassettebox 14 or the outerwall 14a of the cassettebox 14 with material opaque to visible light except for a diagonal strip 14b on one face of the box 14, as illustrated in FIG. 3. Multiple layers of radiographic film are then loaded into the cassettebox 14 so that the planes of the film are perpendicular to the face containing the diagonal strip 14b. Because radiographic film is sensitive to visible light, this arrangement will expose small indexing marks on the edges of the film in the cassettebox 14. This allows for each film to have a uniquely located indexing mark. Determining the location of these exposed indexing marks (specifically, the distance of each mark from the bottom edge of the film) will provide means for automatically orienting and ordering the multiple layers of film and, hence, the multiple dose images developed therefrom. The capacity to automatically orient and order the radiographic film improves the ease of use of the phantom system of the present invention, by eliminating the need to maintain the order of the film during the unloading of the cassettebox and processing of the film.

Next, as indicated in block 54 of FIG. 1, the multiple dose images are combined to form a three-dimensional map of the measured (i.e., actual) dose distributions in the image processing software.

At this time, the multiple dose images may preferably be interpolated therebetween to generate a series of CT-format dose images at an arbitrary spatial frequency, which may be greater than the spatial frequency of the multiple dose images themselves. In other words, a series of CT-format dose images may be obtained to resample the measured dose distributions throughout the entire volume of the multiple layers of film 42. The CT-format dose images can then be transferred to the treatment-planning software, as described above with respect to block 36.

Finally, in block 56 of FIG. 1, the measured three-dimensional dose distribution map obtained in block 54 is spatially coregistered in the treatment-planning software with the intended three-dimensional dose distribution map that was created and registered into the software in block 36. When spatially coregistered, the two dose distribution maps share the same spatial scale, spatial location, and spatial orientation. This permits direct comparison between the measured and intended three-dimensional dose distribution maps.

Based on the coregistration, any inaccuracies included in the intended three-dimensional dose distribution map and, hence, the original stereotactic radiosurgery plan developed in block 36 can be ascertained, prior to the plan's actual application to a patient. Specifically, any discrepancies between the intended and measured dose distributions will reveal inaccuracies inherent in the lesion localization process and the subsequent treatment process. The stereotactic radiosurgery plan can then be adjusted to correct for these inherent inaccuracies.

As briefly noted at the beginning of the present description, the present invention also offers a phantom system for executing the method of the present invention described above. The system comprises a phantom including a hollow shell made of and filled with tissue-equivalent material, a cassettebox adjustably securable within the hollow shell, and multiple layers of film separated by tissue-equivalent spacers, which are removably loaded in the cassettebox. All of these components have been described in detail above.

Clinically, lesions may occur at various locations inside the brain. For example, acoustic neuromas occur near the ear, while nasopharyngeal carcinomas occur at the level of the neck. The design of the anthropomorphic phantom of the present invention permits the multiple layers of film (and the simulated lesion, if one is used) to be positioned anywhere within the hollow shell.

It is noted that many of the steps included in the present simulation method for localizing and treating a lesion as performed on the anthropomorphic film phantom are identical to those performed clinically in localizing and treating an actual lesion. Specifically, the invention may take the image of a simulated lesion while framing the hollow shell containing the lesion with a head ring and a localizer box, and subsequently radiosurgically "treats" the lesion while framing the hollow shell with a head ring and a target-positioner box. The head ring and localizer/target-positioner boxes are equipment widely used in clinical settings. Accordingly, any systematic inaccuracies identified in the present method will also occur in the course of performing stereotactic radiosurgery on a patient. Such inaccuracies may be introduced in the processes of:

(1) localizing (imaging) the lesion;
(2) treatment-planning calculations of intended dose distributions;
(3) setting up of the patient on the linear accelerator couch used in radiosurgery;
(4) aligning of the target positioner box with the isocenter of the linear accelerator; and/or
(5) administering the radiation to the volume of the lesion using the linear accelerator.

Because the method of the present invention encompasses all errors associated with actual localization and treatment of a lesion, the invention provides complete and accurate simulations, which can be reliably used to optimize a stereotactic radiosurgery plan for a clinical application.

The present invention can be used for verification of conventional radiosurgery using circular beams, static conformal radiosurgery using multiple irregular collimators, and static or dynamic radiosurgery using a micromultileaf collimator. Because the system and method of the present invention are completely independent of the method of administering the radiation, they will remain applicable as radiosurgical technology advances.

EXAMPLE

To ensure the validity of the recorded dose, it is crucial that the introduction of radiographic film into the anthropomorphic head phantom does not destroy the tissue equivalence of the phantom in terms of the deposition of dose by the photon beam. This question of tissue equivalence was examined by accurately modeling the phantom using a computer technique called Monte Carlo simulation. This simulation has been established over the years as the most accurate technique for dose calculation. Electron Gamma Shower 4 (EGS4) Monte Carlo simulations have been used to model seventeen adjacent films separated by ⅛" (approximately 3.2 mm) polystyrene spacers. Results of the simulation indicate that presence of the film in the phantom perturbs the deposited dose by less than 1% (compared to the dose deposited within a homogeneous polystyrene phantom without film). This is acceptable in order to guarantee that the dose recorded in the vicinity of the film is sufficiently close to that which would be present without the film.

A series of experiments was conducted to investigate possible dependencies of film sensitivity on field size, depth in a phantom, and film orientation. It has been shown that, for the range of field sizes used in radiosurgery, no significant dependencies exist. Therefore, only a single calibration curve is required to convert the film's optical density to dose.

Also, reproducibility studies have indicated that the production and subsequent measurement of film optical density are reproducible to within, on average, less than 2% between films within one processing session, and to within less than 3% between separate sessions.

While the preferred embodiments of the invention have been illustrated and described, it will be appreciated that various changes can be made therein without departing from the spirit and scope of the invention.

What is claimed is:

1. An anthropomorphic phantom system for recording and verifying three-dimensional dose distributions administered during radiation treatment, the phantom system comprising:
   a hollow shell made of tissue equivalent material and filled with a fluid tissue-equivalent material;
   a box made of tissue-equivalent material mounted within the hollow shell, the box being adapted to be adjustably securable within the hollow shell; and
   multiple layers of film separated by multiple spacers having tissue-equivalent characteristics, the film and spacers being adapted to be loaded into the box,
   wherein the box is vertically adjustable within the hollow shell.

2. The system of claim 1, wherein the hollow shell is formed in the shape of a human head.

3. The system of claim 1, wherein the hollow shell, the box, and the spacers are made of plastic.

4. The system of claim 1, wherein the box is supported by a rod, the rod being slidably adjustable along its axis to vary the position of the box along the axis within the hollow shell.

5. The system of claim 1, wherein the film is radiochromic film.

6. The system of claim 1, wherein the film is radiographic film.

7. The system of claim 1, wherein the hollow shell is filled with water.

8. An anthropomorohic phantom system for recording and verifying three-dimensional dose distributions administered during radiation treatment, the phantom system comprising:
- a hollow shell made of tissue equivalent material and filled with a fluid tissue-equivalent material;
- a box made of tissue-equivalent material mounted within the hollow shell, the box being adapted to be adjustably securable within the hollow shell; and
- multiple layers of film separated by multiple spacers having tissue-equivalent characteristics, the film and spacers being adapted to be loaded into the box, and a simulated lesion replaceably positionable within the box.

9. An anthropomoric phantom system for recording and verifying three-dimensional dose distributions administered during radiation treatment, the phantom system comprising:
- a hollow shell made of tissue equivalent material and filled with a fluid tissue-equivalent material;
- a box made of tissue-equivalent material mounted within the hollow shell, the box being adapted to be adjustably securable within the hollow shell; and
- multiple layers of film separated by multiple spacers having tissue-equivalent characteristics, the film and spacers being adapted to be loaded onto the box, wherein the box is made of material opaque to visible light except for a diagonal strip that is made of material translucent to visible light.

10. An anthropomorphic phantom system for recording and verifying three-dimensional dose distributions administered during radiation treatment, the phantom system comprising:
- a hollow shell made of tissue equivalent material and filled with a fluid tissue-equivalent material;
- a bow made of tissue-equivalent material mounted within the hollow shell, the box being adapted to be adjustably securable within the hollow shell; and
- multiple layers of film separated by multiple spacers having tissue-equivalent characteristics, the film and spacers being adapted to be loaded into the box, wherein the box is horizontally adjustable within the hollow shell.

11. An anthropomorphic phantom system for recording and verifying three-dimensional dose distributions administered during radiation treatment, the phantom system comprising:
- a hollow shell made of tissue equivalent material and filled with a fluid tissue-equivalent material;
- a box made of tissue-equivalent material mounted within the hollow shell, the box being adapted to be adjustably securable within the hollow shell; and
- multiple layers of film separated by multiple spacers having tissue-equivalent characteristics, the film and spacers being adapted to be loaded into the box, wherein the box is adjustable so as to vary its angular orientation with respect to the hollow shell.

12. A method of recording and verifying three-dimensional dose distributions administered during radiation treatment, the method comprising:
(a) providing a phantom including a hollow shell made of a tissue equivalent material and filled with a fluid tissue-equivalent material, the hollow shell being adapted to simulate a human head, the hollow shell including a box made of tissue-equivalent material, the box being adjustably securable within the hollow shell;
(b) registering an image of a lesion to be treated including its position with respect to the hollow shell in software;
(c) in the software, developing a radiation treatment plan based on the image of the lesion, the radiation treatment plan including an intended three-dimensional dose distribution man;
(d) loading multiple layers of film separated by multiple spacers having tissue-equivalent characteristics into the box;
(e) delivering radiation according to the radiation treatment plan to the hollow shell including the box containing the multiple layers of film;
(f) removing the multiple layers of film from the box;
(g) obtaining multiple dose images based on the multiple layers of film;
(h) forming a three-dimensional map of a measured dose distribution using the multiple dose images; and
(i) coregistering the three-dimensional map of the measured dose distribution with the intended three-dimensional dose distribution map in the software to ascertain any inaccuracies included in the radiation treatment plan, wherein steps (d) through (f) are repeated for a prescribed number of times, with each repetition varying an angular orientation of the box with respect to the hollow shell, to obtain plural sets of multiple layers of film, to which the radiation is delivered.

13. The method of claim 12, wherein step (b) further comprises:
(i) placing a simulated lesion that models the lesion to be treated within the box, filling the box with tissue-equivalent material, and securing the box at a predetermined position with respect to the hollow shell;
(ii) taking an image of the hollow shell including the box containing the simulated lesion;
(iii) removing the box from the hollow shell and removing the simulated lesion from the box.

14. The method of claim 13, wherein step (ii) further comprises placing a head ring on the hollow shell and coupling a localizer box to the head ring.

15. The method of claim 12, wherein step (e) further comprises placing a head ring on the hollow shell and coupling a target-positioner box to the head ring.

16. The method of claim 12, wherein the hollow shell is formed in the shape of a human head.

17. A method of claim 12, wherein step (h) further comprises interpolating the multiple dose images to generate a series of computed tomography-format dose images.

18. A method of recording and verifying three-dimensional dose distributions administered during radiation treatment, the method comprising:
(a) providing a phantom including a hollow shell made of a tissue equivalent material and filled with a fluid tissue-equivalent material, the hollow shell being adapted to simulate a human head, the hollow shell including a box made of tissue-equivalent material, the box being adjustably securable within the hollow shell;
(b) registering an image of a lesion to be treated including its position with respect to the hollow shell in software;
(c) in the software, developing a radiation treatment plan based on the image of the lesion, the radiation treatment plan including an intended three-dimensional dose distribution map;
(d) loading multiple layers of film separated by multiple spacers having tissue-equivalent characteristics into the box;

(e) delivering radiation according to the radiation treatment plan to the hollow shell including the box containing the multiple layers of film;

(f) removing the multiple layers of film from the box;

(g) obtaining multiple dose images based on the multiple layers of film;

(h) forming a three-dimensional man of a measured dose distribution using the multiple dose images; and (i) coregistering the three-dimensional map of the measured dose distribution with the intended three-dimensional dose distribution man in the software to ascertain any inaccuracies included in the radiation treatment plan wherein the box is opaque to visible light except for a diagonal strip that is made of a material translucent to visible light, and step (g) further comprises automatically ordering and orienting the multiple layers of film based upon an indexing mark uniquely recorded on an edge of each of the multiple layers of film by light passing through the diagonal strip.

19. An anthropomorphic film phantom system for recording and verifying three-dimensional dose distributions administered during radiation treatment, the film phantom system being adapted to be replaceably mounted inside a hollow shell that is made of a tissue-equivalent material and filled with a fluid tissue-equivalent material to simulate a human head; the film phantom system comprising:

a box made of tissue-equivalent material adapted to be adjustably securable within the hollow shell; and multiple layers of film separated by multiple spacers having tissue-equivalent characteristics, the film and spacers being adapted to be loaded into the box;

wherein the box is opaque to visible light except for a diagonal strip that is made of material translucent to visible light.

20. The system of claim 19, wherein the box and the spacers are made of plastic.

21. The system of claim 19, wherein the film is radiochromic film.

22. The system of claim 19, wherein the film is radiographic film.

23. A film phantom system for recording and verifying three-dimensional dose distributions, the film phantom system comprising:

a box made of tissue-equivalent material; and multiple spacers having tissue-equivalent characteristics, the spacers being adapted to be loaded into the box together with multiple layers of film separated by the spacers;

wherein the box is opaque to visible light except for a diagonal strip that is translucent to visible light.

24. A film phantom system according to claim 23, wherein the diagonal strip crosses edges of the multiple layers of film when the spacers are loaded into the box together with the multiple layers of film.

* * * * *